United States Patent
Brandt et al.

(10) Patent No.: US 10,231,777 B2
(45) Date of Patent: Mar. 19, 2019

(54) METHODS OF MANUFACTURING JAW MEMBERS OF AN END-EFFECTOR ASSEMBLY FOR A SURGICAL INSTRUMENT

(71) Applicant: COVIDIEN LP, Mansfield, MA (US)

(72) Inventors: Kim V. Brandt, Loveland, CO (US); Monte S. Fry, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 343 days.

(21) Appl. No.: 14/793,978

(22) Filed: Jul. 8, 2015

(65) Prior Publication Data

US 2016/0058497 A1 Mar. 3, 2016

Related U.S. Application Data

(60) Provisional application No. 62/041,871, filed on Aug. 26, 2014.

(51) Int. Cl.
*A61B 18/14* (2006.01)
*B29C 70/68* (2006.01)
(Continued)

(52) U.S. Cl.
CPC ...... *A61B 18/1445* (2013.01); *B29C 45/0025* (2013.01); *B29C 45/16* (2013.01);
(Continued)

(58) Field of Classification Search
CPC ........ A61B 18/1445; A61B 2018/1455; A61B 2017/00526; A61B 2018/0063;
(Continued)

(56) References Cited

U.S. PATENT DOCUMENTS

| | | | |
|---|---|---|---|
| 371,664 A | 10/1887 | Brannan et al. | |
| 702,472 A | 6/1902 | Pignolet | |

(Continued)

FOREIGN PATENT DOCUMENTS

| | | |
|---|---|---|
| EP | 2620118 A2 | 7/2013 |
| EP | 2687176 A1 | 1/2014 |

(Continued)

OTHER PUBLICATIONS

U.S. Appl. No. 12/336,970, filed Dec. 17, 2008, Sremcich, Abandoned.

(Continued)

*Primary Examiner* — Michael N Orlando
*Assistant Examiner* — Cynthia L Schaller

(57) ABSTRACT

A method of manufacturing a jaw member of an end-effector assembly includes forming one or more stress-relief cavities within a sealing plate. Each one of the one or more stress-relief cavities defines a pad portion of an electrically-conductive surface of the sealing plate. The method also includes forming a stop member on each pad portion of the electrically-conductive surface of the sealing plate, performing an overmolding operation wherein the one or more stress-relief cavities is configured to prevent force applied to a bottom surface of the sealing plate during the overmolding operation from stressing each pad portion to avoid compromising adhesion between the stop member and the electrically-conductive surface of the sealing plate.

7 Claims, 6 Drawing Sheets

(51) Int. Cl.
*B29C 45/16* (2006.01)
*B29C 45/00* (2006.01)
*B29L 31/00* (2006.01)
*A61B 17/00* (2006.01)
*A61B 18/00* (2006.01)
*A61B 17/29* (2006.01)
*B29C 70/88* (2006.01)

(52) U.S. Cl.
CPC .. *B29C 70/683* (2013.01); *A61B 2017/00526* (2013.01); *A61B 2017/2926* (2013.01); *A61B 2018/0063* (2013.01); *A61B 2018/1455* (2013.01); *B29C 70/882* (2013.01); *B29C 2045/1695* (2013.01); *B29L 2031/7546* (2013.01)

(58) Field of Classification Search
CPC .......... A61B 2017/2926; B29C 70/683; B29C 45/0025; B29C 45/16; B29C 70/882; B29C 2045/1695; B29L 2031/7546
See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,279,753 A | 4/1942 | Knopp |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,088,134 A | 5/1978 | Mazzariello |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| 4,311,145 A | 1/1982 | Esty et al. |
| D263,020 S | 2/1982 | Rau III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| D298,353 S | 11/1988 | Manno |
| D299,413 S | 1/1989 | DeCarolis |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,047,046 A | 9/1991 | Bodoia |
| 5,084,057 A | 1/1992 | Green et al. |
| 5,085,659 A | 2/1992 | Rydell |
| 5,099,840 A | 3/1992 | Goble et al. |
| 5,104,410 A | 4/1992 | Chowdhary |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,102 A | 3/1993 | Arterbury et al. |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| D343,453 S | 1/1994 | Noda |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,304,203 A | 4/1994 | El-Mallawany et al. |
| 5,308,357 A | 5/1994 | Lichtman |
| 5,313,027 A | 5/1994 | Inoue et al. |
| 5,314,445 A | 5/1994 | Heidmueller nee Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| D349,341 S | 8/1994 | Lichtman et al. |

(56) References Cited

U.S. PATENT DOCUMENTS

| | | |
|---|---|---|
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| D354,564 S | 1/1995 | Medema |
| 5,383,875 A | 1/1995 | Bays et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,409,763 A | 4/1995 | Serizawa et al. |
| D358,887 S | 5/1995 | Feinberg |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Shame et al. |
| 5,509,922 A | 4/1996 | Aranyi et al. |
| 5,512,721 A | 4/1996 | Young et al. |
| 5,514,134 A | 5/1996 | Rydell et al. |
| 5,527,313 A | 6/1996 | Scott et al. |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,699 A | 10/1996 | Heimberger et al. |
| 5,562,720 A | 10/1996 | Stern et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,584,845 A | 12/1996 | Hart |
| 5,585,896 A | 12/1996 | Yamazaki et al. |
| 5,590,570 A | 1/1997 | LeMaire, III et al. |
| 5,597,107 A | 1/1997 | Knodel et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,688,270 A | 11/1997 | Yates et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| H1745 H | 4/1998 | Paraschac |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,701 A | 7/1998 | McBrayer et al. |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |

(56) References Cited

U.S. PATENT DOCUMENTS

| | | |
|---|---|---|
| 5,810,877 A | 9/1998 | Roth et al. |
| 5,814,043 A | 9/1998 | Shapeton |
| 5,817,093 A | 10/1998 | Williamson, IV et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| D402,028 S | 12/1998 | Grimm et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,882,567 A | 3/1999 | Cavallaro et al. |
| D408,018 S | 4/1999 | McNaughton |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,935,126 A | 8/1999 | Riza |
| 5,941,869 A | 8/1999 | Patterson et al. |
| 5,944,718 A | 8/1999 | Austin et al. |
| 5,951,546 A | 9/1999 | Lorentzen |
| 5,951,549 A | 9/1999 | Richardson et al. |
| 5,954,720 A | 9/1999 | Wilson et al. |
| 5,957,923 A | 9/1999 | Hahnen et al. |
| 5,960,544 A | 10/1999 | Beyers |
| 5,961,514 A | 10/1999 | Long et al. |
| 5,964,758 A | 10/1999 | Dresden |
| D416,089 S | 11/1999 | Barton et al. |
| 5,976,132 A | 11/1999 | Morris |
| 5,984,938 A | 11/1999 | Yoon |
| 5,984,939 A | 11/1999 | Yoon |
| 5,989,277 A | 11/1999 | LeMaire, III et al. |
| 5,997,565 A | 12/1999 | Inoue |
| 6,004,335 A | 12/1999 | Vaitekunas et al. |
| 6,010,516 A | 1/2000 | Hulka |
| 6,024,741 A | 2/2000 | Williamson, IV et al. |
| 6,024,743 A | 2/2000 | Edwards |
| 6,024,744 A | 2/2000 | Kese et al. |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Van De Moer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan, Jr. |
| 6,302,424 B1 | 10/2001 | Gisinger et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| D453,923 S | 2/2002 | Olson |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| D465,281 S | 11/2002 | Lang |
| D466,209 S | 11/2002 | Bon |
| 6,485,489 B2 | 11/2002 | Teirstein et al. |
| 6,500,176 B1 | 12/2002 | Truckai et al. |
| 6,508,815 B1 | 1/2003 | Strul et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |

(56) References Cited

U.S. PATENT DOCUMENTS

| | | |
|---|---|---|
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,641,776 B1 | 11/2003 | Weaver et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,669,696 B2 | 12/2003 | Bacher et al. |
| 6,673,092 B1 | 1/2004 | Bacher |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,857,357 B2 | 2/2005 | Fujii |
| D502,994 S | 3/2005 | Blake, III |
| 6,860,880 B2 | 3/2005 | Treat et al. |
| 6,887,240 B1 | 5/2005 | Lands et al. |
| 6,908,463 B2 | 6/2005 | Treat et al. |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,987,244 B2 | 1/2006 | Bauer |
| 6,988,318 B2 | 1/2006 | Buchtmann et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,274 S | 12/2006 | Visconti et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sailor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| D538,932 S | 3/2007 | Malik |
| 7,195,631 B2 | 3/2007 | Dumbauld |
| D541,418 S | 4/2007 | Schechter et al. |
| 7,207,990 B2 | 4/2007 | Lands et al. |
| D541,611 S | 5/2007 | Aglassinger |
| D541,938 S | 5/2007 | Kerr et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |

(56) References Cited

U.S. PATENT DOCUMENTS

| | | |
|---|---|---|
| 7,344,268 B2 | 3/2008 | Jigamian |
| RE40,273 E | 4/2008 | Grace, Jr. et al. |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,265 B2 | 7/2008 | Darley et al. |
| 7,396,356 B2 | 7/2008 | Mollenauer |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,491,201 B2 | 2/2009 | Shields et al. |
| 7,491,202 B2 | 2/2009 | Odom et al. |
| 7,668,597 B2 | 2/2010 | Engmark et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,877,852 B2 | 2/2011 | Unger et al. |
| 7,913,402 B2 | 3/2011 | Buchtmann et al. |
| 7,931,649 B2 | 4/2011 | Couture et al. |
| 8,016,827 B2 | 9/2011 | Chojin |
| D649,249 S | 11/2011 | Guerra |
| D649,643 S | 11/2011 | Allen, IV et al. |
| 8,114,122 B2 | 2/2012 | Nau, Jr. |
| 8,142,473 B2 | 3/2012 | Cunningham |
| 8,162,973 B2 | 4/2012 | Cunningham |
| 8,197,479 B2 | 6/2012 | Olson et al. |
| 8,226,650 B2 | 7/2012 | Kerr |
| 8,251,999 B2 | 8/2012 | Stearns et al. |
| 8,257,387 B2 | 9/2012 | Cunningham |
| 8,266,783 B2 | 9/2012 | Brandt et al. |
| 8,282,634 B2 | 10/2012 | Cunningham et al. |
| 8,303,582 B2 | 11/2012 | Cunningham |
| 8,317,787 B2 | 11/2012 | Hanna |
| 8,329,803 B2 | 12/2012 | Evstatieva et al. |
| 8,382,792 B2 | 2/2013 | Chojin |
| 8,469,956 B2 | 6/2013 | McKenna et al. |
| 8,469,957 B2 | 6/2013 | Roy |
| 8,486,107 B2 | 7/2013 | Hinton |
| 8,535,312 B2 | 9/2013 | Horner |
| 8,623,276 B2 | 1/2014 | Schmaltz et al. |
| 8,632,539 B2 | 1/2014 | Twomey et al. |
| 8,632,564 B2 | 1/2014 | Cunningham |
| 8,636,761 B2 | 1/2014 | Cunningham et al. |
| 8,764,748 B2 | 7/2014 | Chojin |
| 8,784,417 B2 | 7/2014 | Hanna |
| 8,795,274 B2 | 8/2014 | Hanna |
| 8,864,202 B1 * | 10/2014 | Schrameyer ...... H01L 21/68707 294/213 |
| 8,968,314 B2 | 3/2015 | Allen, IV |
| 9,192,427 B2 | 11/2015 | Johnson et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0216733 A1 | 11/2003 | McClurken et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sartor et al. |
| 2004/0199181 A1 | 10/2004 | Knodel et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0260281 A1 | 12/2004 | Baxter et al. |
| 2005/0004564 A1 | 1/2005 | Wham et al. |
| 2005/0004569 A1 | 1/2005 | Witt et al. |
| 2005/0021026 A1 | 1/2005 | Baily |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0141355 A1 | 6/2006 | Darley et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |

(56) References Cited

U.S. PATENT DOCUMENTS

| | | |
|---|---|---|
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0208289 A1 | 8/2008 | Darley et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319046 A1 | 12/2008 | Hu |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088744 A1 | 4/2009 | Townsend |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0209960 A1 | 8/2009 | Chojin |
| 2009/0254081 A1 | 10/2009 | Allison et al. |
| 2010/0042143 A1 | 2/2010 | Cunningham |
| 2010/0069903 A1 | 3/2010 | Allen, IV et al. |
| 2010/0069953 A1 | 3/2010 | Cunningham et al. |
| 2010/0076427 A1 | 3/2010 | Heard |
| 2011/0073246 A1* | 3/2011 | Brandt ............... A61B 18/1445 156/242 |
| 2011/0178519 A1 | 7/2011 | Couture et al. |
| 2013/0079774 A1 | 3/2013 | Whitney et al. |
| 2013/0331837 A1 | 12/2013 | Larson |
| 2014/0217521 A1* | 8/2014 | Johari-Galle ....... B81C 1/00134 257/415 |
| 2016/0035593 A1* | 2/2016 | Read ..................... H01L 21/565 438/127 |

FOREIGN PATENT DOCUMENTS

| | | |
|---|---|---|
| EP | 2687177 A2 | 1/2014 |
| WO | 02080796 A1 | 10/2002 |

OTHER PUBLICATIONS

U.S. Appl. No. 12/400,901, filed Mar. 10, 2009, McKenna, Abandoned.

U.S. Appl. No. 12/195,624, filed Aug. 21, 2008, Cartlton, Abandoned.

U.S. Appl. No. 12/204,976, filed Sep. 5, 2008, Giuliani, Abandoned.

EP Search Report for Application No. 15 182 267 dated Jan. 26, 2016.

* cited by examiner

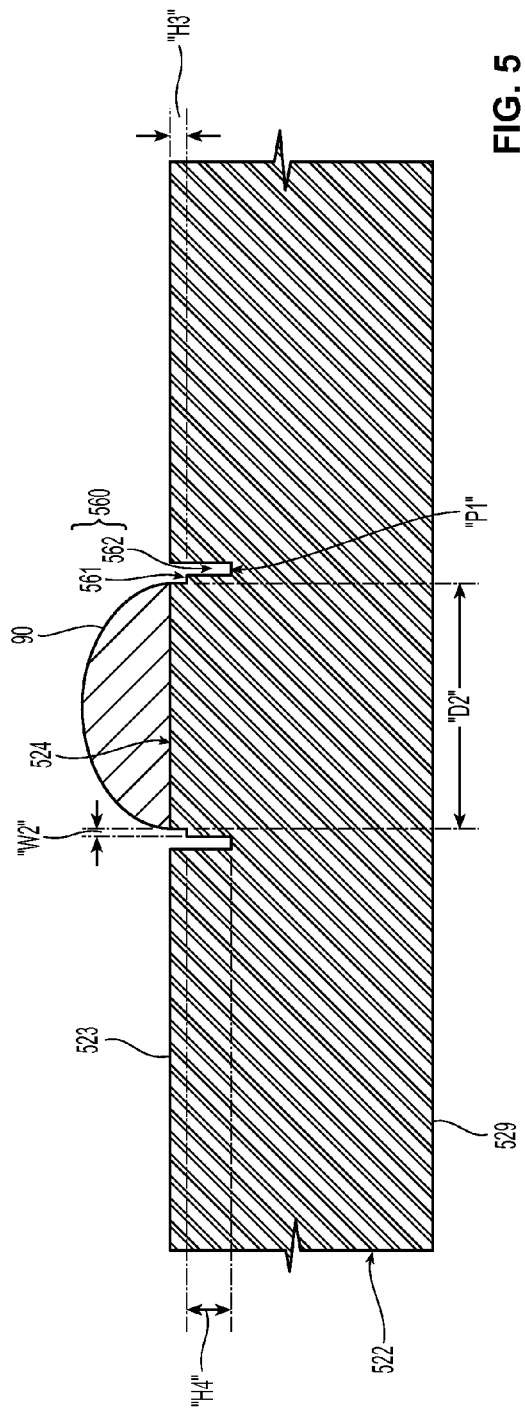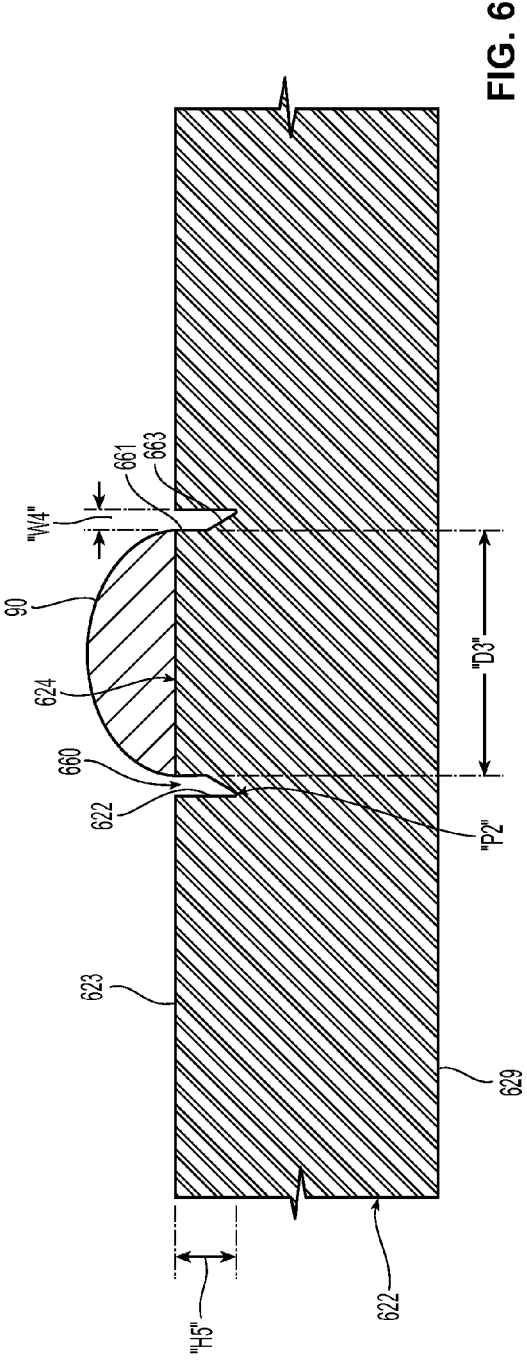

METHODS OF MANUFACTURING JAW MEMBERS OF AN END-EFFECTOR ASSEMBLY FOR A SURGICAL INSTRUMENT

CROSS REFERENCE TO RELATED APPLICATION

The present application claims the benefit of and priority to U.S. Provisional Application Ser. No. 62/041,871, filed on Aug. 26, 2014, the entire contents of which are incorporated herein by reference.

BACKGROUND

1. Technical Field

The present disclosure relates to the field of surgical instruments. More particularly, the disclosure relates to methods of manufacturing jaw members of an end-effector assembly for a surgical instrument.

2. Discussion of Related Art

Bipolar electrosurgical forceps have an end-effector assembly with electrodes on the inner, opposing surfaces of pivotally movable jaw members. The electrodes are electrically coupled to an electrosurgical generator, with the electrode on one jaw member actively delivering electrosurgical energy and the electrode on the other jaw member functioning as a return, thereby creating an electrical circuit through tissue grasped by the jaw members.

Tissue grasped by the jaw members can be treated to different degrees (e.g., cauterized, coagulated, desiccated, sealed, or divided) depending on the intensity, frequency and duration of the electrosurgical energy applied by the electrodes. The effectiveness of the electrosurgical energy on the tissue is affected by mechanical factors such as the pressure applied to the tissue when grasped by the jaw members and the gap distance between the electrically-conductive tissue-contacting surfaces (electrodes) of the jaw members.

Predictability in such mechanical factors can be provided by meeting specific tolerance requirements when manufacturing the end-effector assembly of the electrosurgical forceps. It would be desirable to develop manufacturing methods for end-effector assemblies to meet tolerance requirements such as gap tolerances, alignment of the jaw members and the like. It would be desirable to develop manufacturing methods for jaw members to ensure the reliability of stop members for controlling the gap distance between the electrically-conductive tissue-contacting surfaces of the jaw members when closed about tissue.

SUMMARY

Jaw members that meet design tolerance requirements and ensure the reliability of stop members for controlling the gap distance are provided by the manufacturing processes described herein.

According to an aspect of the present disclosure, a method of manufacturing a jaw member of an end-effector assembly is provided and includes forming one or more stress-relief cavities within a sealing plate. Each one of the one or more stress-relief cavities defines a pad portion of an electrically-conductive surface of the sealing plate. The method also includes forming a stop member on each pad portion of the electrically-conductive surface of the sealing plate, performing an overmolding operation, wherein the one or more stress-relief cavities is configured to prevent force applied to a bottom surface of the sealing plate during the overmolding operation from stressing the pad portion to avoid compromising adhesion between the stop member and the electrically-conductive surface of the sealing plate.

According to another aspect of the present disclosure, a method of manufacturing a jaw member of an end-effector assembly is provided and includes forming at least one stress-relief cavity within a sealing plate. Each one of the at least one stress-relief cavities defines a pad portion of an electrically-conductive surface of the sealing plate. The method also includes: depositing a material on each pad portion for forming a stop member thereon, each one of the at least one stress-relief cavities functioning as a wetting ring to limit the spread of the material; and utilizing each one of the at least one stress-relief cavities to prevent force applied to a bottom surface of the sealing plate during an overmolding operation from stressing each pad portion to avoid compromising adhesion between the stop member and the electrically-conductive surface of the sealing plate.

In any one of the preceding aspects, forming one or more stress-relief cavities may include forming a first portion of each of the one or more stress-relief cavities configured to facilitate the formation of a stop member having a circle-like shape or oval-like shape.

In any one of the preceding aspects, forming one or more stress-relief cavities includes forming a second portion of each of the one or more stress-relief cavities configured to prevent stress from external forces applied to the sealing plate from compromising adhesion between the stop member and the sealing plate.

BRIEF DESCRIPTION OF THE DRAWINGS

Objects and features of the end-effector assemblies for use in surgical instruments and methods of manufacturing jaw members of an end-effector assembly of the present disclosure will become apparent to those of ordinary skill in the art when descriptions of various embodiments thereof are read with reference to the accompanying drawings, of which:

FIG. 5 is a cross-sectional view of a portion of a sealing plate including a stress-relief cavity defined therein in accordance with an embodiment of the present disclosure;

FIG. 6 is a cross-sectional view of a portion of a sealing plate including a stress-relief cavity defined therein in accordance with another embodiment of the present disclosure.

DETAILED DESCRIPTION

Figure 1:
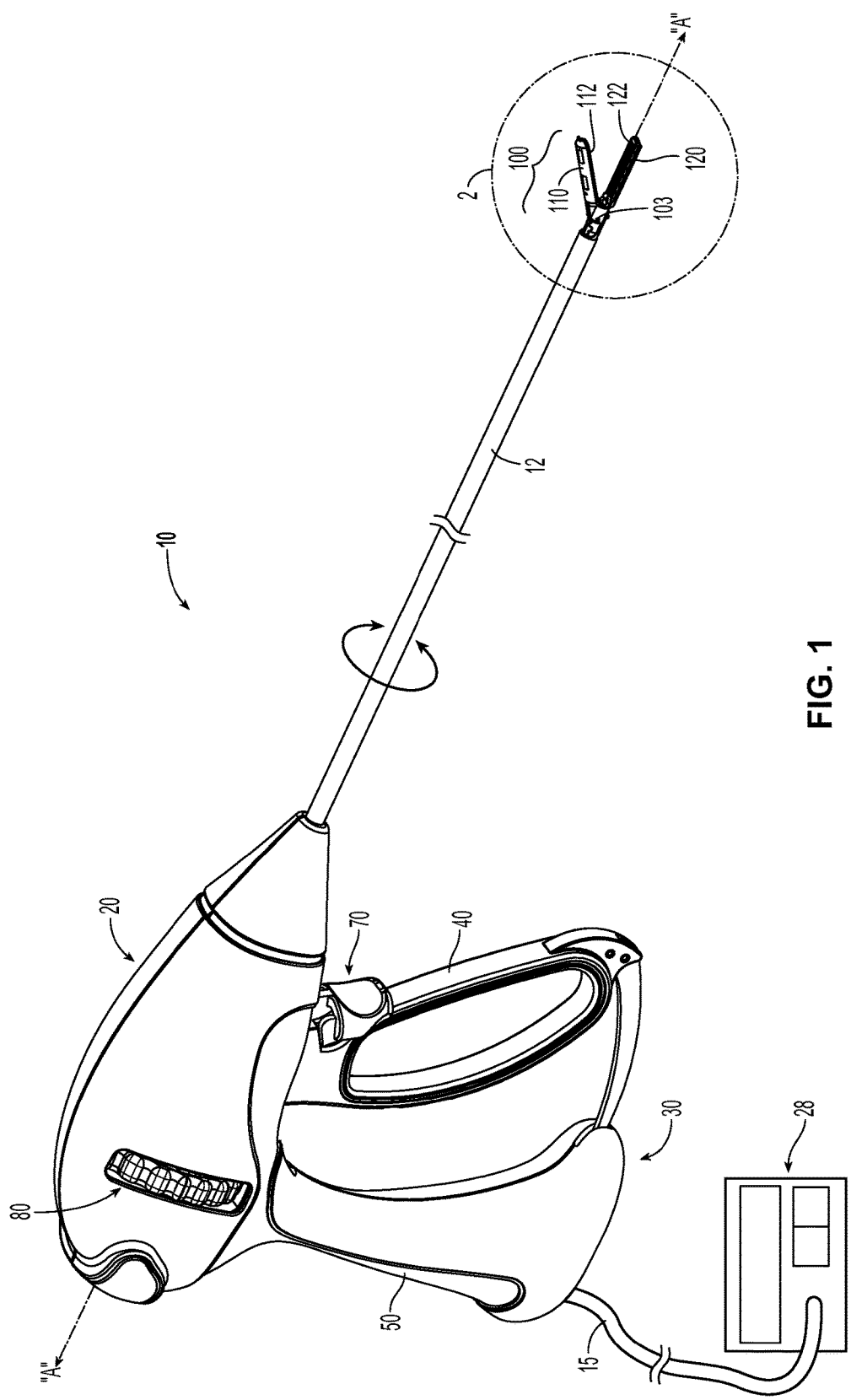
FIG. 1 is a perspective view of a surgical instrument in accordance with an embodiment of the present disclosure.

Hereinafter, embodiments of end-effector assemblies for use in surgical instruments and methods of manufacturing jaw members of an end-effector assembly of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

As it is used in this description, "electrically-conductive tissue-contacting plate" generally refers to an electrically-conductive member including one or more tissue engaging surfaces that can be used to transfer energy from an electrosurgical power generating source, such as RF electrosurgical generator, to tissue. As it is used in this description, "electrically conductive", or simply "conductive", generally refers to materials that are capable of electrical conductivity, including, without limitation, materials that are highly conductive, e.g., metals and alloys, or materials that are semi-conductive, e.g., semi-conducting materials and composites.

Vessel sealing or tissue sealing utilizes a combination of radiofrequency energy, pressure and gap control to effectively seal or fuse tissue between two opposing jaw members or sealing plates thereof. Vessel or tissue sealing is more than "cauterization" which may be defined as the use of heat to destroy tissue (also called "diathermy" or "electrodiathermy"), and vessel sealing is more than "coagulation" which may be defined as a process of desiccating tissue wherein the tissue cells are ruptured and dried. As it is used in this description, "vessel sealing" generally refers to the process of liquefying the collagen, elastin and ground substances in the tissue so that it reforms into a fused mass with significantly-reduced demarcation between the opposing tissue structures.

Various embodiments of the present disclosure provide end-effector assemblies for use in surgical instruments, e.g., surgical forceps, suitable for sealing, cauterizing, coagulating/desiccating and/or cutting vessels and vascular tissue. Various embodiments of the present disclosure provide methods of manufacturing jaw members of an end-effector assembly. Embodiments of the presently-disclosed methods of manufacturing jaw members include forming one or more stress-relief cavities within one or both of the electrically-conductive tissue-engaging surfaces of the opposing pair of jaw members.

In FIG. 1, a surgical instrument generally identified as forceps 10 is shown for use with various surgical procedures and includes a housing 20, a handle assembly 30, a rotatable assembly 80, a trigger assembly 70, and an end-effector assembly 100 including opposing jaw members 110 and 120. Handle assembly 30 includes a fixed handle 50 and a movable handle 40. One or more components of the forceps 10, e.g., the housing 20, the rotatable assembly 80, the handle assembly 30, the trigger assembly 70, and/or the end-effector assembly 100 may be adapted to mutually cooperate to grasp, seal and/or divide tissue, e.g., tubular vessels and vascular tissue. Forceps 10 may include additional, fewer, or different components than shown in FIG. 1, depending upon a particular purpose or to achieve a desired result.

Figure 2:
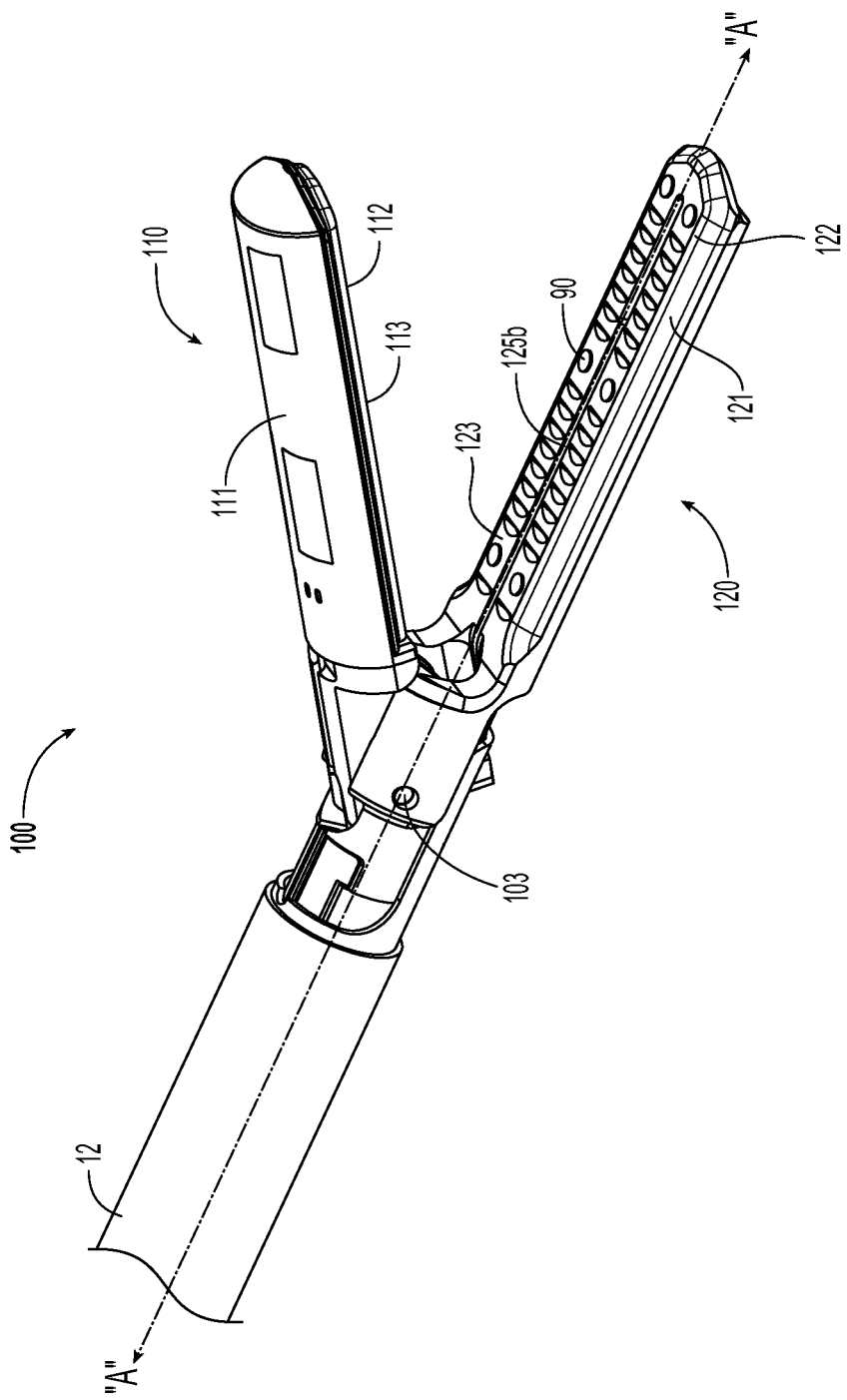
FIG. 2 is a perspective view of the indicated area of detail of FIG. 1.

As shown in FIGS. 1 and 2, the jaw members 110 and 120 include an electrically-conductive tissue-engaging surface 112 and 122, respectively, arranged in opposed relation relative to one another. One or both of the jaw members 110 and 120 include one or more stress-relief cavities (e.g., the stress-relief cavity 160 shown in FIGS. 3, 4A and 4B, the stress-relief cavity 560 shown in FIG. 5, or the stress-relief cavity 660 shown in FIG. 6) defined within one or both of the electrically-conductive tissue-engaging surfaces 112 and 122 (also referred to herein as "sealing plates 112 and 122").

Forceps 10 generally includes an elongated shaft 12 that defines a longitudinal axis "A-A", and supports the end-effector assembly 100. Shaft 12 extends from the housing 20 and supports movement of other components therethrough, e.g., to impart movement to the jaw members 110 and 120. End-effector assembly 100 is rotatable about the longitudinal axis "A-A" through rotation, either manually or otherwise, of the rotatable assembly 80. As shown in FIG. 1, rotation of the rotatable assembly 80 rotates the elongated shaft 12 which, in turn, rotates the end-effector assembly 100 in the clockwise or counter-clockwise direction to manipulate and grasp tissue. Although FIG. 1 depicts an electrosurgical forceps for use in connection with endoscopic surgical procedures, the teachings of the present disclosure may also apply to more traditional open surgical procedures.

As shown in FIGS. 1 and 2, the end-effector assembly 100 is configured as a unilateral assembly that includes a stationary jaw member (e.g., jaw member 120) mounted in fixed relation to the shaft 12 and a pivoting jaw member (e.g., jaw member 110) movably mounted about a pivot pin 103 coupled to the stationary jaw member 120. Jaw members 110 and 120 may be curved at various angles to facilitate manipulation of tissue and/or to provide enhanced line-of-sight for accessing targeted tissues. End-effector assembly 100 may include one or more electrically-insulative elements to electrically isolate the pivoting jaw member 110 from the stationary jaw member 120 and/or to isolate both or one of the jaw members 110 and 120 from the shaft 12. Alternatively, the end-effector assembly 100 may be configured for bilateral movement, i.e., both jaw members 110 and 120 are moveable relative to one another.

As can be appreciated, applying force to move the movable handle 40 toward the fixed handle 50 pulls a drive sleeve or drive rod (not shown) proximally to impart movement to the jaw members 110 and 120 from an open position, wherein the jaw members 110 and 120 are disposed in spaced relation relative to one another, to a clamping or closed position, wherein the jaw members 110 and 120 cooperate to grasp tissue therebetween. Trigger assembly 70 is operable to extend and retract a knife blade through the end-effector assembly 100 when the end-effector assembly 100 is in the closed configuration.

Forceps 10 includes a cable 15, which is in electrical communication with at least one of the jaw members 110 and 120 such that electrosurgical energy, e.g., supplied by a power generating source 28, may be delivered to tissue clamped in the end-effector assembly 100. Cable 15 may be internally divided into one or more cable leads each of which transmits energy through its respective feed path to the end-effector assembly 100. Power generating source 28 may be any generator suitable for use with surgical devices, and may be configured to operate in a variety of modes. Forceps 10 may alternatively be configured as a wireless device or battery-powered.

Sealing plates 112 and 122, as shown in FIG. 2, have a tissue-engaging surface 113 and 123, respectively. One or both of the sealing plates 112 and 122 may define a longitudinally-extending knife channel (e.g., knife channel 125b shown in FIG. 2). The shape and size of the sealing plates 112 and 122 may be varied from the configuration depicted in FIGS. 1 and 2.

In some embodiments, the end-effector assembly 100 may include a structural support member (not shown) associated with each of the jaw members 110 and 120 and configured to support the sealing plates 112 and 122. Support structures may be formed from any suitable material or combination of materials, e.g., metallic material, plastic and the like, and may be formed by any suitable process, e.g., machining, stamping, electrical discharge machining (EDM), forging, casting, injection molding, metal injection molding (MIM), and/or fineblanking. Examples of metallic material that may be suitable include aluminum and alloys thereof, plated brass, stainless steel, stainless steel alloys, beryllium copper, etc. End-effector assembly 100 may include electrically-insulative members and/or electrically-insulative, thermally non-degrading coatings configured to electrically isolate, at least in part, the sealing plates 112 and 122 from the structural support members.

Figure 3:
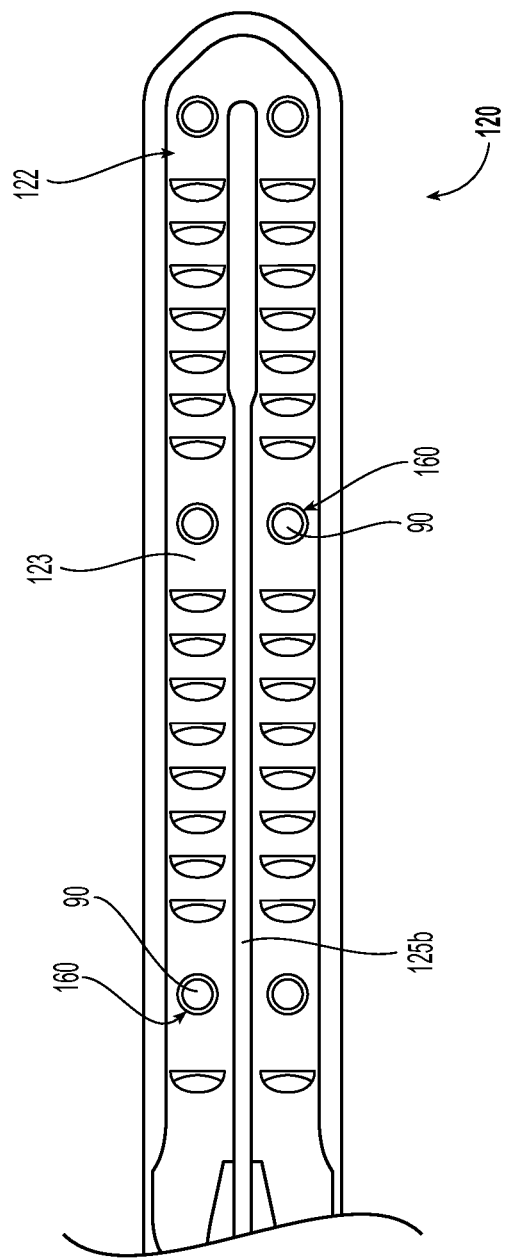
FIG. 3 is a schematic diagram illustrating a top view of the sealing plate of a jaw member of the end-effector assembly of FIG. 2 in accordance with an embodiment of the present disclosure.

In some embodiments, as shown for example in FIGS. 2 and 3, the jaw member 120 includes a series of electrically non-conductive stop members 90 disposed on the tissue-engaging surface 123 of the sealing plate 122. Alternatively or in addition, one or more non-conductive stop members 90 may be associated with the jaw member 110, e.g., disposed on the tissue-engaging surface 113 of the sealing plate 112. Circle-like stop members 90 shown in FIGS. 2 and 3 are substantially equal in size; however, one or more of the stop members 90 may be dimensioned larger or smaller than the other stop members 90 depending upon a particular purpose or to achieve a desired result.

Stop members 90 may be configured to facilitate and/or enhance the gripping and manipulation of tissue and to control the gap distance between the electrically-conductive sealing plates 112 and 122 of the jaw members 110 and 120, respectively, when closed about tissue, e.g., during the sealing and cutting of tissue. In some embodiments, to provide an effective tissue seal, an appropriate gap distance of about 0.001 inches to about 0.010 inches and, desirably, between about 0.002 inches to about 0.005 inches, may be provided. Stop members 90 of varied configurations may be disposed on or adjacent to one or both of the sealing plates 112 and 122 and/or operatively associated with one or both jaw members 110 and 120, e.g., depending upon a particular purpose or to achieve a desired result.

In some embodiments, the sealing plates 112 and 122 may be at least partially encapsulated by outer insulative housings (e.g., outer housing 111 and 121 shown in FIG. 2) by way of an overmolding process. Outer housings 111 and 121 may define a cavity (not shown) therein configured to at least partially encapsulate and/or securely engage the sealing plates 112 and 122, respectively, and/or other jaw member components. In some embodiments, the outer housings 111 and 121 may be made from an electrically and thermally insulating material, e.g., a temperature resistant plastic or a ceramic, overmolded onto the sealing plates 112 and 122, respectively.

Stress-relief cavities 160 of varied configurations may be associated with one or both of the sealing plates 112 and 122. In some embodiments, as shown for example in FIG. 3, the sealing plate 122 includes a plurality of stress-relief cavities 160. Each one of the plurality of stress-relief cavities 160 is disposed about a different one of the stop members 90. Although the stop members 90 have a circle-like shape and the stress-relief cavities 160 have a ring-like shape, other shapes may be utilized.

Figure 4A:
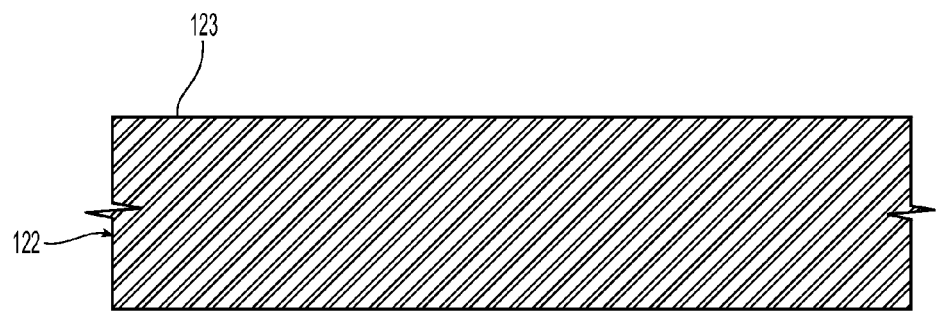
FIGS. 4A through 4C show a schematic representation of a sequence of operations of a method of manufacturing jaw members in accordance with an embodiment of the present disclosure.
Figure 4B:
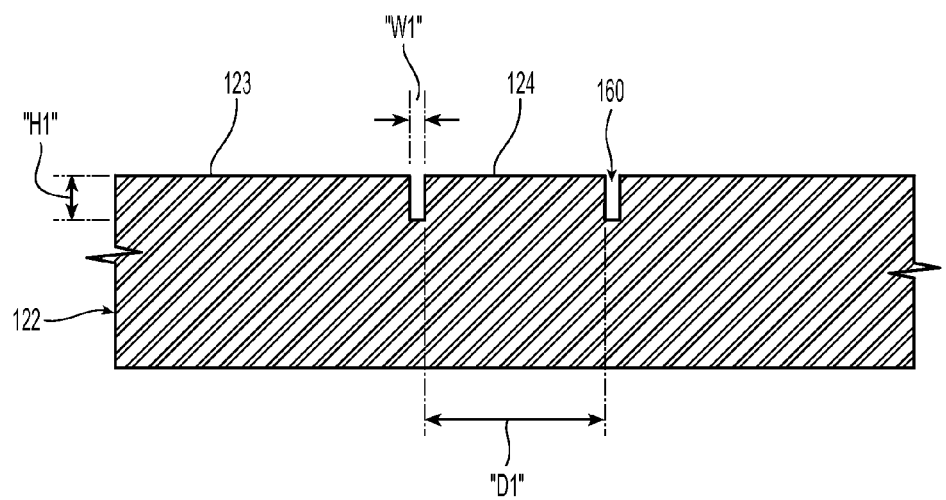
Figure 4C:
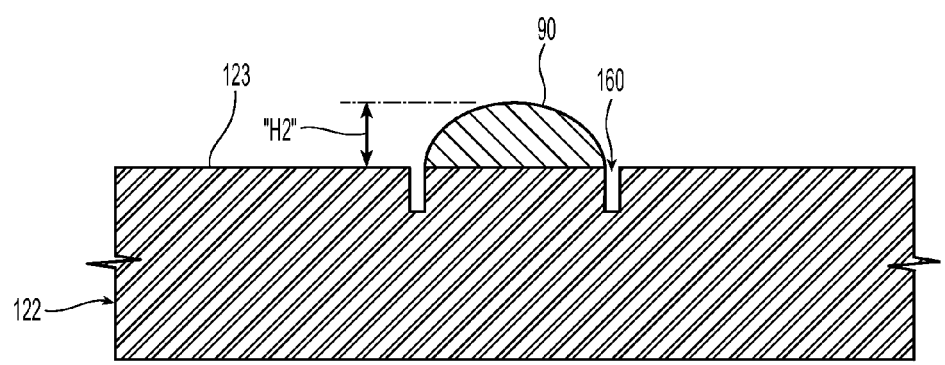

FIGS. 4A through 4C schematically illustrate a series of operations according to a method of manufacturing jaw members. One or more of the operations depicted in the illustrative embodiment of FIGS. 4A through 4C may be performed in combination without departing from the scope of the disclosure. The operations, which are described in more detail below, generally involve the formation of a sealing plate (e.g., sealing plate 122), the formation of one or more stress-relief cavities 160, and the formation of one or more stop members 90.

In accordance with a method of manufacturing jaw members of the present disclosure, in an initial step, as shown in FIG. 4A, a sealing plate (e.g., sealing plate 122) is provided. Sealing plates 112 and 122 may be formed from any suitable material or combination of materials, e.g., metallic material, and may be formed by any suitable process, e.g., machining, stamping, electrical discharge machining (EDM), forging, casting, injection molding, metal injection molding (MIM), and/or fineblanking. One or more electrical leads (not explicitly shown) may be electrically-coupled by any suitable manner, e.g., soldering, welding, or laser welding, to either one or both of the sealing plates 112 and 122.

FIG. 4B shows a stress-relief cavity 160 disposed within the sealing plate 122. In accordance with methods of manufacturing jaw members of the present disclosure, one or more stress-relief cavities 160 are formed within the sealing plate 122 (and/or sealing plate 112) prior to depositing, or otherwise forming, the stop members 90. Stress-relief cavities 160 may be formed by any suitable process, and may have any suitable depth (generally referred to herein as "height H1") relative the surface 123 of the sealing plate 122, and any suitable width "W1". In some embodiments, the stress-relief cavities 160 may be formed by one or more of etching, machining, stamping, and fineblanking.

Stress-relief cavities 160 are configured to facilitate the formation of the stop members 90 and configured to prevent stress from external forces applied to the seal plate from compromising the adhesion of the stop members 90 during an overmolding operation, e.g., overmolding of an outer insulative housing of a jaw member. An illustrative embodiment of an overmolding operation performed on a sealing plate configured with a stress-relief cavity (e.g., stress-relief cavity 660 shown in FIG. 6) is described later in this disclosure with reference to FIG. 7.

As shown in FIG. 4B, the stress-relief cavity 160 cuts into the tissue-engaging surface 123 of the sealing plate 122 and thereby defines a pad portion 124. Pad portion 124 is configured to facilitate the formation of a stop member 90 in a particular shape, e.g., a circle-like shape. Pad portion 124 may be configured to function as a wetting ring, e.g., to limit the spread of a viscous material applied to the surface 123 of the sealing plate 122 during the formation of the stop member 90. Pad portion 124 may have any suitable configuration, e.g., diameter "D1", depending on the location, size, and/or shape of the stop member 90. Sealing plate 122 may be configured with any suitable number of stress-relief cavities 160 and pad portions 124.

FIG. 4C shows a stop member 90 having any suitable height "H2" disposed on the pad portion 124. In some embodiments, the stop members 90 may be affixed and/or attached to one or both of the jaw members 110 and 120 by stamping, thermal spraying, overmolding, and/or by an adhesive. In some variations of stop members, compatible with any of the embodiments disclosed herein, stop members may be printed, patterned, applied, or otherwise deposited using a direct write process, such as by a micro-capillary system, or any other suitable material deposition technology.

In some embodiments, a high-velocity oxygen fuel (HVOF) spraying process, or any other suitable thermal spray process, may be used to form the stop members 90.

In some embodiments, the stop members 90 are constructed of a heat-resistant ceramic deposited onto one or both of the sealing plates 112 and 122. Stop members 90 may define any suitable number, arrangement, and/or configuration, to achieve a desired gap distance, e.g., depending on a particular purpose. In some embodiments, upon depositing a ceramic (or any other suitable material) onto the sealing plate 122 to form a plurality of stop members 90, the stress-relief cavities 160 function as wetting rings to provide shape uniformity among the plurality of stop members 90.

FIG. 5 shows a portion of a sealing plate 522 including a stress-relief cavity 560 defined therein. Stress-relief cavity 560 may be formed by any suitable process, e.g., etching, machining, stamping, and/or fineblanking. Sealing plate 522 includes a tissue-engaging surface 523 and is similar to the sealing plate 122 of FIGS. 1 through 3, except for the different configurations of the stress-relief cavity 160 of FIG. 1 and the stress-relief cavity 560 shown in FIG. 5. Further description of like elements is omitted in the interests of brevity.

Stress-relief cavity 560 includes a first portion 561 having any suitable height "H3" and any suitable width "W2". As shown in FIG. 5, the first portion 561 defines a pad portion 524 of the sealing plate 522, e.g., configured to facilitate the formation of a stop member 90 in a particular shape, e.g., a circle-like shape. Pad portion 524 may have any suitable diameter "D2". First portion 561 of the stress-relief cavity 560 is configured to function as a wetting ring, e.g., to provide shape uniformity among a plurality of stop members 90.

Because of the high pressures utilized during overmolding of jaw members, force applied to the bottom surface 529 of the sealing plate 522 can result in bending and/or deflection the tissue-engaging surface 523 of the sealing plate 522. Stress-relief cavity 560 includes a second portion 562 having any suitable height "H3"+"H4" and configured to prevent stress from external forces applied to the sealing plate 522 (e.g., during an overmolding operation) from compromising the adhesion between the stop member 90 and the sealing plate 522.

In accordance with an embodiment of the present disclosure, the bottom of the second portion 562 provides a stress-relief point "P1" that is offset from the pad portion 524 of the sealing plate 522. The configuration of the stress-relief point "P1" shown in FIG. 5 eliminates or minimizes stresses on the pad portion 524, e.g., during overmolding, to ensure that adhesion of the stop member 90 is not compromised.

FIG. 6 shows a portion of a sealing plate 622 including a stress-relief cavity 660 defined therein. Sealing plate 622 is similar to the sealing plate 122 of FIGS. 1 through 3, except for the different configurations of the stress-relief cavity 160 of FIG. 1 and the stress-relief cavity 660 shown in FIG. 5. Further description of like elements is omitted in the interests of brevity.

Stress-relief cavity 660 is defined by a first wall 661, a second wall 662, and a third wall 663. The first wall 661 of the stress-relief cavity 660 defines a pad portion 624 of the sealing plate 622. Pad portion 624 is configured to facilitate the formation of a stop member 90 in a particular shape, e.g., a circle-like shape. Pad portion 624 may have any suitable diameter "D3".

The second wall 662 of the stress-relief cavity 660 may have any suitable height "H5". As shown in FIG. 6, the third wall 663 slopes upwardly from the bottom of the second wall 662 to the bottom of the first wall 661. The bottom of the second wall 662 provides a stress-relief point "P2" that is offset from the first wall 661, which defines the pad portion 624 of the sealing plate 622. The configuration of the stress-relief point "P2" shown in FIG. 6 eliminates or minimizes stresses on the pad portion 624 (e.g., during overmolding, deflection takes place at the stress-relief point "P2") to ensure that adhesion between the stop member 90 and the sealing plate 622 is not compromised.

Figure 7:
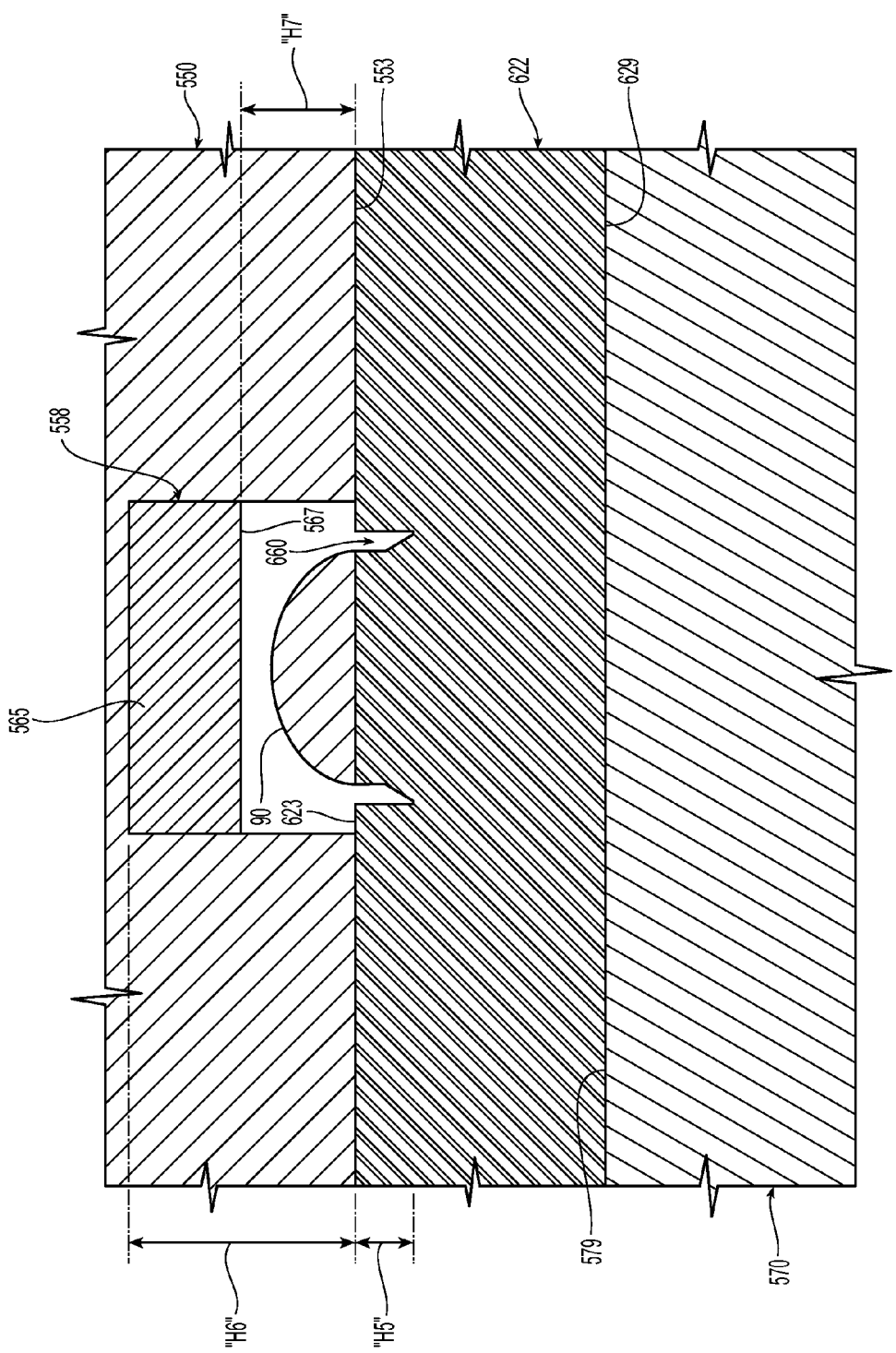
FIG. 7 is a cross-sectional view of a portion of a mold tool for use in the manufacture of jaw members, showing the mold tool in engagement with the sealing plate of FIG. 6, in accordance with an embodiment of the present disclosure.

In FIG. 7, a first tool member 550 and a second tool member 570 are shown for use in the overmolding of jaw members and compatible with any of the sealing plate embodiments disclosed herein. As shown in FIG. 7, a surface 579 of the second tool 570 is disposed in contact with the bottom surface 629 of the sealing plate 622, and a surface 553 of the tool member 550 is disposed in contact with the tissue-engaging surface 623 of the sealing plate 622.

First tool member 550 includes a cavity 558 having any suitable height "H6". A material 565 is disposed within a portion of the cavity 558, wherein the material includes a surface 567 that is offset by a suitable height "H7" from the surface 553 of the first tool member 550. The height "H7" may be set to minimize the risk of any contact between the stop member 90 and the material 565 upon deflection of the sealing plate during the overmolding process. Material 565 may be any material having suitable material characteristics. In some embodiments, the material 565 may be sufficiently resilient to absorb impact with the stop member 90 upon deflection of the sealing plate, e.g., to prevent cracking or otherwise damaging the stop member 90.

In accordance with an embodiment of the present disclosure, compatible with any of the sealing plate embodiments disclosed herein, a method of manufacturing a pair of opposing jaw members 110 and 120 of an end-effector assembly 100 includes forming one or more stress-relief cavities (e.g., stress-relief cavity 560) within a sealing plate (e.g., sealing plate 522). Each of the one or more stress-relief cavities 560 defines a pad portion 524 of an electrically-conductive surface 523 of the sealing plate 522. The method also includes forming a stop member 90 on each pad portion 524 of the electrically-conductive surface 523 of the sealing plate 522, performing an overmolding operation, and utilizing the one or more stress-relief cavities 560 to prevent force applied to a bottom surface 529 of the sealing plate 522 during the overmolding operation from stressing each pad portion 524 to avoid compromising adhesion between the stop member 90 and the electrically-conductive surface 523 of the sealing plate 522.

In a slight variation of FIG. 7 (not shown), the inner edge of the stress relief cavity 560 (660) is configured or shaped to reduce coining of the seal plate 522 (622) by the cavity 560 (660) when subjected to molding pressures.

The above-described end-effector assembly embodiments including any combination of features of the above-described sealing plates may utilize jaw member components of varied geometries, e.g., lengths and curvatures, such that variously-configured jaw members may be fabricated and assembled into various end-effector configurations, e.g., depending upon design of specialized surgical instruments.

The above-described surgical instrument embodiments may also be configured to work with robotic surgical systems and what is commonly referred to as "Telesurgery." Such systems employ various robotic elements to assist the surgeon in the operating theater and allow remote operation (or partial remote operation) of surgical instrumentation.

Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Although embodiments have been described in detail with reference to the accompanying drawings for the purpose of illustration and description, it is to be understood that the disclosed processes and apparatus are not to be construed as limited thereby. It will be apparent to those of ordinary skill in the art that various modifications to the foregoing embodiments may be made without departing from the scope of the disclosure.

What is claimed is:

1. A method of manufacturing a jaw member of an end-effector assembly, comprising:
    forming at least one stress-relief cavity in an electrically-conductive surface of a sealing plate, each one of the at least one stress-relief cavities defining a pad portion having a pad surface coincident with the remainder of the electrically-conductive surface of the sealing plate; and
    depositing a material on the pad surface of each pad portion to form a stop member thereon, each pad portion surrounded by one of the at least one stress-relief cavities, each one of the at least one stress-relief cavities functioning as a wetting ring to limit the spread of the material, wherein each one of the at least one stress-relief cavities is configured to prevent force applied to a bottom surface of the sealing plate during an overmolding operation from stressing each pad portion to avoid compromising adhesion between the stop member and the pad surface of the electrically-conductive surface of the sealing plate.

2. The method of claim 1, wherein depositing a material on each pad portion includes depositing a heat-resistant ceramic on each pad portion.

3. The method of claim 1, wherein forming the at least one stress-relief cavity within the sealing plate includes forming at least one stress-relief cavity including a first portion configured to function as a wetting ring.

4. The method of claim 3, wherein forming the at least one stress-relief cavity within the sealing plate further includes forming at least one stress-relief cavity including a second portion configured to provide a stress-relief point that is offset from the pad portion.

5. The method of claim 1, wherein forming the at least one stress-relief cavity within the sealing plate includes forming at least one stress-relief cavity that is defined by a first wall, a second wall, and a third wall.

6. The method of claim 5, wherein forming the at least one stress-relief cavity that is defined by the first wall, the second wall, and the third wall includes the first wall defining the pad portion.

7. The method of claim 6, wherein forming the at least one stress-relief cavity that is defined by the first wall, the second wall, and the third wall includes providing a stress-relief point at a bottom of the second wall that is offset from the first wall by the third wall.

* * * * *